United States Patent [19]

Umezawa et al.

[11] Patent Number: 4,745,067

[45] Date of Patent: May 17, 1988

[54] L-AMINOACYLASES

[75] Inventors: Hamao Umezawa; Tomio Takeuchi, both of Tokyo; Toshiharu Nagatsu, Yokohama; Masa Hamada; Shuichi Iwadare, both of Tokyo; Ikuo Matsumoto; Hajime Morishima, both of Tokyo, all of Japan

[73] Assignees: Microbial Chemistry Research Foundation; Banyu Pharmaceutical Co., Ltd., both of Tokyo, Japan

[21] Appl. No.: 857,941

[22] Filed: Apr. 29, 1986

[30] Foreign Application Priority Data

May 2, 1985 [JP] Japan .................................. 60-93769
Mar. 18, 1986 [JP] Japan .................................. 61-58192

[51] Int. Cl.$^4$ ........................ C12N 9/80; C12P 13/00; C07B 19/02; C12R 1/04; C12R 1/465; C12R 1/52; C12R 1/625

[52] U.S. Cl. .................................. 435/228; 435/280; 435/128; 435/886; 435/826; 435/893; 435/908

[58] Field of Search ........................ 435/228, 128, 280

[56] References Cited

U.S. PATENT DOCUMENTS 3,838,008 9/1974 Bamberg et al. .............. 435/228 X

FOREIGN PATENT DOCUMENTS 60-160895 8/1985 Japan .................................. 435/128

Primary Examiner—Lionel M. Shapiro
Attorney, Agent, or Firm—Oblon, Fisher, Spivak, McClelland & Maier

[57] ABSTRACT

L-aminoacylases $S_1$ and $S_2$ derived from actinomycetes and having physicochemical characteristics such that it is a L-aminoacylase which acts on a N-acyl-L-amino acid to give a L-amino acid, its substrate profile is wide, and it acts not only on a N-acyl derivative of a natural L-amino acid, but also on a N-acyl derivative of a synthetic L-amino acid, while it does not act on a N-acyl-D-amino acid, a DL-N-acetyl-α-methylbenzylamine and a N-acetyl-D-glucosamine, etc.

3 Claims, 9 Drawing Sheets

L-AMINOACYLASES

The present invention relates to L-aminoacylases which are useful in a wide range for the production of optically active amino acids useful for foods, medicines, feeds and other industrial materials.

As an enzyme which catalyzes a reaction of a N-acyl-L-amino acid to give a L-amino acid, a hog kidney aminoacylase is known as derived from an animal (Methods in Enzymolozy, Vol. 2, p109 (1955)). Further, it is known that such enzymes derived from microorganisms are widely distributed in various strains such as *Lactobacillus arabinosus* (Park R. W. et al, Journal of Biological Chemistry, Vol. 235, p3193 (1960)), Corynebacterium (Okuta et al, Japanese Examined Patent Publication No. 13989/1974), Aspergillus and Rhizopus families (Chihara et al, Bulletin of the Agricultural Chemical Society of Japan, Vol. 21, No. 5, p304–307 (1957); Solodovnikora, N. I. et al, Inst. Biosin, Belkovykh Veshchesto, Vol 1, p145-151 (1972)). However, those practically employed for the industrial purposes, are restricted to fungal amino acid acylases from the viewpoint of costs. Aminoacylases which are commercially available at present, include Acylase Amano (manufactured by Amano Seiyaku), Acylase Tokyo Kasei (manufactured by Tokyo Kasei) and Acylase I (manufactured by Miles Laboratory).

Conventional fungal aminoacylases such as Acylase Amano are known to hydrolyze usual amino acids, for example, N-acyl derivatives such as L-methionine and L-phenylalanine. However, they do not act on special synthetic amino acids such as L-threo-N-acetyl-3-(3,4-dibenzyloxyphenyl)serine, whereby it is not possible to obtain L-threo-3-(3,4-dibenzyloxyphenyl)serine which is useful as an intermediate for the synthesis of a curing agent for Parkinson disease.

The present inventors have conducted extensive researches on various microorganisms including known strains to obtain a L-aminoacylase having a substrate profile wider than the conventional L-aminoacylases, and have finally found that a certain actinomycete produces L-aminoacylase $S_1$ and L-aminoacylase $S_2$ each having a substrate profile wider than the conventional L-aminoacylases.

The present invention provides L-aminoacylase $S_1$ derived from an actinomycete and having the following physicochemical characteristics:

(1) Action and substrate profile

It is a L-aminoacylase which acts on a N-acyl-L-amino acid to give a L-amino acid, its substrate profile is wide, and it acts not only on a N-acyl derivative of a natural L-amino acid, but also on a N-acyl derivative of a synthetic L-amino acid, while it does not act on a N-acyl-D-amino acid, a DL-N-acetyl-α-methylbenzylamine and a N-acetyl-D-glucosamine, (2) Stability Temperature: it maintains its activity almost fully at 50° C., and a slight activity remains even at 60° C. (when left for one hour at pH 7.0), pH: it is most stable at pH 7.0–9.0, and relatively stable even at about pH 10.0, but it loses its activity at pH 4.0 or lower (when left for 24 hours at 5° C.).

(3) Temperature- and pH-dependence

Temperature: its activity increases linearly up to 50° C., and it loses its reactivity rapidly at a temperature of 60° C. or higher, pH: its reactivity is high at pH 6.5–9.5 and the optimum pH for the reaction is about pH 7.5–8.5, (4) Molecular weight: 50,000–60,000 (gel-filtration method)

(5) Isoelectric point: pI=7.00–7.70, (6) Disc gel electrophoresis: $R_mBPB=0.125-0.167$ (7) Influence of metal ions It is strongly inhibited by $Fe^{++}$, $Ni^{++}$, $Ag^+$, $Hg^{++}$ and $Cu^{++}$, and it is activated by $Co^{++}$, (8) Inhibitor It is inhibited by p-chloromercuribenzoate, it is not inhibited by monoiodoacetic acid, and it is moderately inhibited by ethylenediaminetetraacetate; and L-aminoacylase $S_2$ derived from an actinomycete and having the following physicochemical characteristics:

(1) Action and substrate profile

It is a L-aminoacylase which acts on a N-acyl-L-amino acid to give a L-amino acid, its substrate profile is wide, and it acts not only on N-acyl derivative of a natural L-amino acid, but also on a N-acyl derivative of a synthetic L-amino acid, while it does not act on a N-acyl-D-amino acid, a DL-N-acetyl-α-methylbenzylamine and a N-acetyl-D-glucosamine, (2) Stability Temperature: it does not lose its activity up to 50° C., maintains 80% of the activity at 60° C., and at least 20% of the activity remains even at 70° C. (when left for 10 minutes at pH 7.0), pH: it is most stable at pH 8.5–10.0, and 50% of the activity remains even at about pH 3.5 and at about pH 11.0 (when left for 24 hours at 5° C.), (3) Temperature - and pH-dependence Temperature: its relative activity increases linearly up to 60° C., and it maintains at least 70% of the reactivity even at 70° C., pH: its reactivity is high at pH 7.0–10.0, the optimum pH for the reaction is about pH 8.0–9.0.

(4) Molecular weight: 50,000 to 60,000 (gel-filtration method), (5) Isoelectric point: pI=6.38–7.42

(6) Disc gel electrophoresis: $R_mBPB=0.180-0.280$ (7) Influence of metal ions

It is strongly inhibited by $Cu^{++}$, $Mn^{++}$, $Co^{++}$, $Hg^{++}$, $Fe^{++}$, $Ni^{++}$ and $Ag^+$, (8) Inhibitor It is strongly inhibited by p-chloromercuribenzoate, L-cysteine and monoiodoacetic acid, but it is scarcely inhibited by ethylenediaminetetraacetate.

Now, the present invention will be described in detail with reference to the preferred embodiments.

In the accompanying drawings.

Firstly, the physicochemical characteristics of L-aminoacylase $S_1$ of the present invention will be described.

(1) Substrate profile

The enzymatic activity was measured by using N-acyl derivatives of various amino acids as the substrate. The relative activity based on L-N-acetyl-methionine being evaluated to be 100 is shown in Table 1.

TABLE 1

Substrate profile

| Substrate | Relative activity (%) |
|---|---|
| L-N—acetyl-methionine | 100 |
| L-N—formyl-methionine | 4 |
| D-N—acetyl-methionine | 0 |
| N—acetyl-glycine | 2 |
| L-N—acetyl-alanine | 7 |
| L-N—acetyl-valine | 42 |
| L-N—acetyl-leucine | 76 |
| L-N—acetyl-tryptophan | 80 |
| D-N—acetyl-tryptophan | 0 |
| L-N—acetyl-phenylalanine | 197 |
| L-N—acetyl-glutamic acid | 19 |
| L-N—acetyl-histidine | 41 |
| L-N—acetyl-arginine | 85 |
| L-threo-N—acetyl-3-(3,4-dibenzyloxyphenyl)serine | 14 |
| L-N—acetyl-2-(4-hydroxymethyl-3-hydroxyphenyl)glycine | 41 |
| DL-N—acetyl-α-methylbenzylamine | 0 |
| N—acetyl-D-glucosamine | 0 |

As is evident from Table 1, L-aminoacylase $S_1$ of the present invention acts on N-acyl derivatives of a wide range of L-amino acids including special synthetic amino acids, and has a substrate profile wider than the conventional L-aminoacylases. Usually, acylases act on such acyl groups as an acetyl group and a chloroacetyl group, but they rarely hydrolyze a benzoyl group. Some acylases produced by a certain group of bacteria selectively cleave benzoyl groups, but in such a case, they do not hydrolyze e.g. acetyl groups. L-aminoacylase $S_1$ of the present invention shows a wide substrate profile for various acyl groups, and while it is most effective to cleave an acetyl group or a chloroacetyl group, but it is also effective to readily cleave a benzoyl group.

(2) Thermal stability

Figure 1:
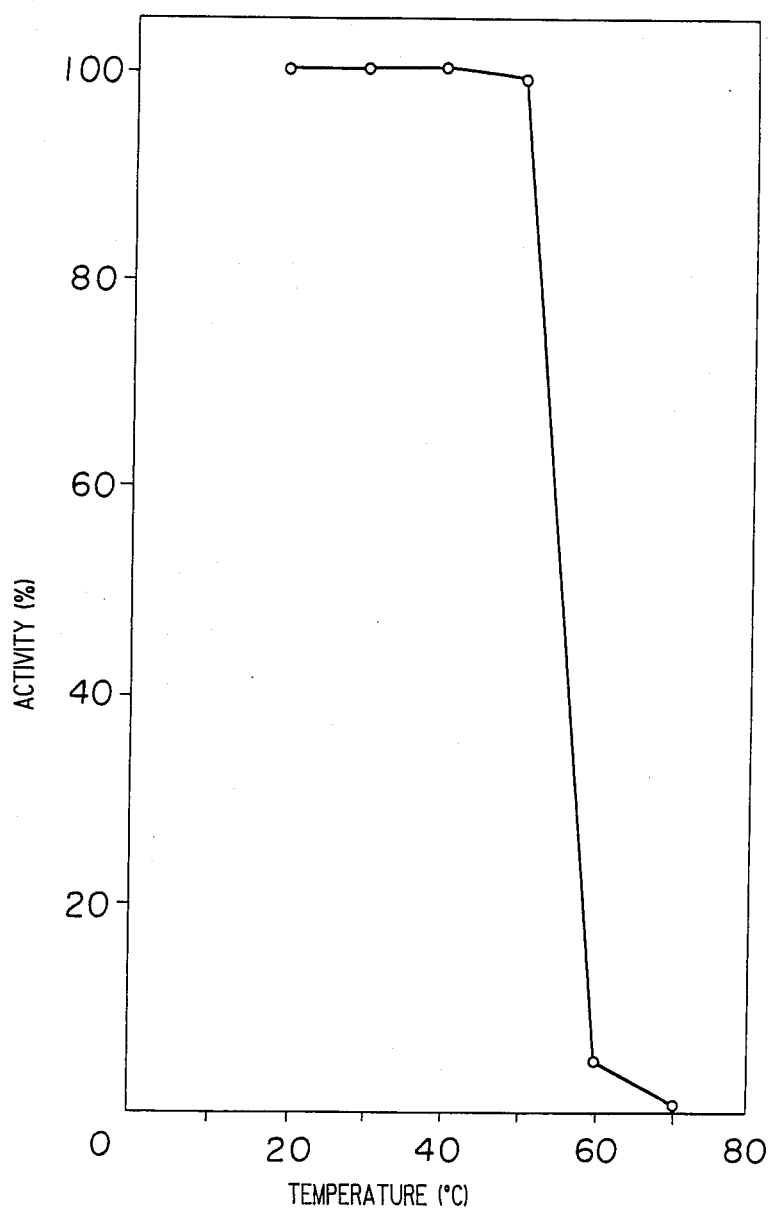
FIG. 1 shows the thermal stability of L-aminoacylase $S_1$ of the present invention.
Figure 2:
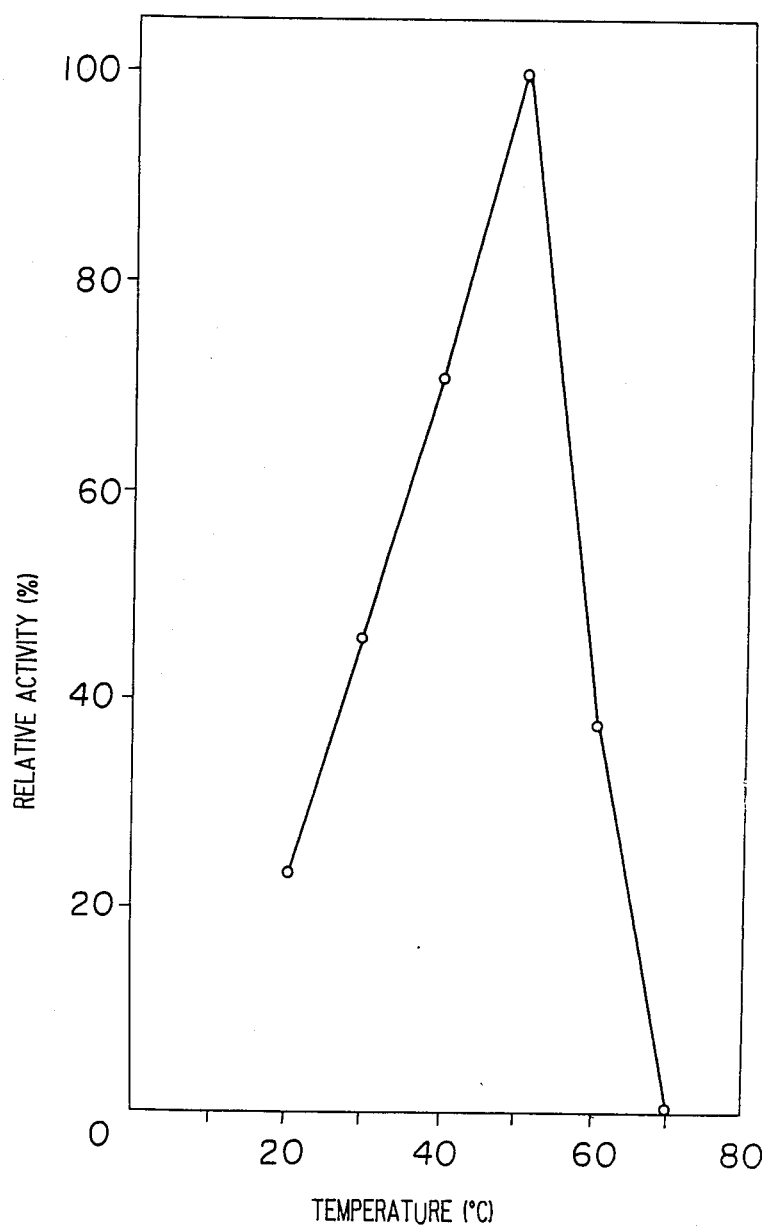
FIG. 2 shows its reaction temperature (the optimum temperature).

A potassium phosphate buffer solution (pH 7.0) of the enzyme of the present invention was treated for one hour at various temperatures, and the remaining activity was measured. As the substrate, L-threo-N-acetyl-3-(3,4-dibenzyloxyphenyl)serine (hereinafter referred to simply as N-Ac-DB-DOPS) was employed, and the reaction was conducted at 37° C. for one hour, whereupon freed L-threo-3-(3,4-dibenzyloxyphenyl)serine (hereinafter referred to simply as DB-DOPS) was measured by a ninhydrin method to determine the activity. The results of measurements are shown in FIG. 1. As shown, 95% or more is deactivated by the treatment at pH 7.0 at 60° C., but the enzyme is certainly stable at a temperature of 50° C. or lower.

(3) Temperature-dependence

L-aminoacylase $S_1$ of the present invention was reacted in a potassium phosphate buffer solution (pH 7.0) with N-Ac-DB-DOPS as the substrate for one hour at various temperatures, whereby the relative activity was measured in the above-mentioned method. The results are shown in Table 2. Like acylases, its reactivity increases linearly up to about 50° C. i.e. the limit for deactivation, and the activity will rapidly be lost at a temperature higher than 50° C.

(4) pH stability

Figure 3:
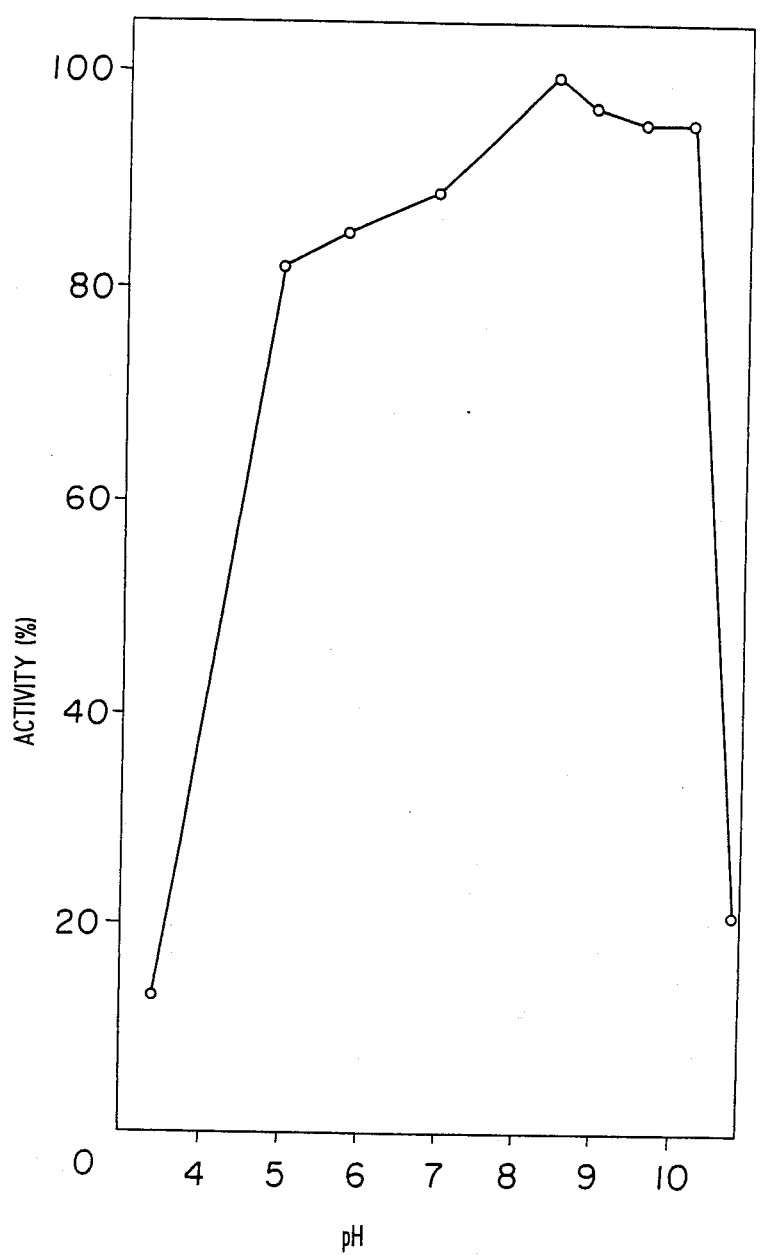
FIG. 3 shows its pH stability.

The enzyme solution of the present invention was left to stand at 5° C. for 24 hours at various pH conditions. Then, each solution was adjusted to pH 7.0 and reacted with N-Ac-DB-DOPS as the substrate at 37° C. for one hour, whereby the remaining activity was measured by the above-mentioned method. The results are shown in FIG. 3.

L-aminoacylase $S_1$ of the present invention is most stable under a weakly basic condition i.e. at pH 7.0–9.0, and is relatively stable even at about pH 10.0.

(5) pH-dependence

Figure 4:
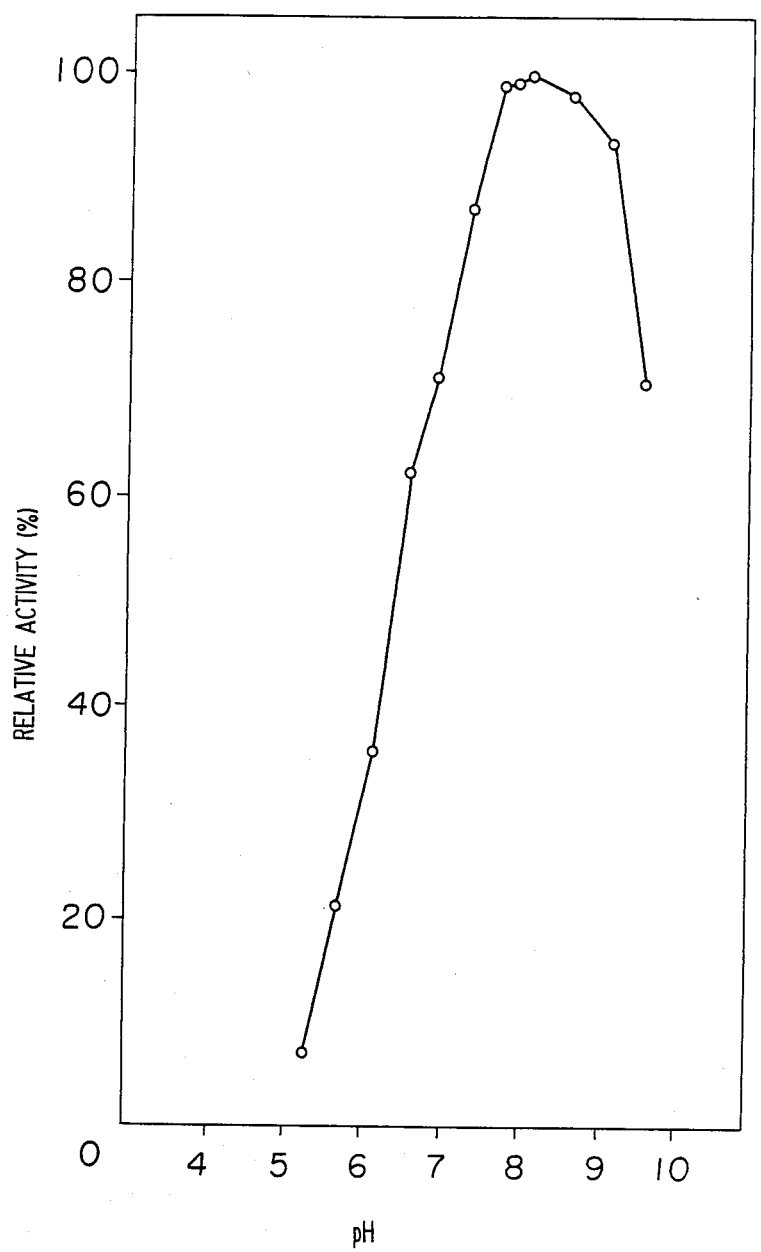
FIG. 4 shows its reaction pH (optimum pH).

The enzyme of the present invention was reacted at a temperature of 37° C. under various pH conditions with N-Ac-DB-DOPS as the substrate for one hour, whereby the relative activity was measured by the above-mentioned method. The results are shown in FIG. 4. L-aminoacylase $S_1$ of the present invention is highly reactive at pH 7.0–10.0, and the optimum pH is from about 7.5 to about 8.5.

(6) Molecular weight

The molecular weight of the enzyme of the present invention was measured by a gel-filtration method of Sephadex G-100 ® (manufactured by Pharmacia Company). The molecular weight of L-aminoacylase $S_1$ of the present invention is within a range of from 50,000 to 60,000 Dalton. As the standard protein samples, cytochrome C (molecular weight: 12,500), carbonic anhydrase (molecular weight: 29,000), egg white albumin (molecular weight: 45,000) and bovine serum albumin (molecular weight: 67,000) were used.

(7) Isoelectric point

The isoelectric point was measured at 4° C. by applying 800 V for two hours by using Anpholine PAG ® plate (manufactured by LKB Company). As opposed to the conventional aminoacylases being usually acidic proteins, the isoelectric point (pI) of the enzyme of the present invention is within a range of from 7.0 to 7.7, thus indicating that the enzyme of the present invention is a basic protein.

(8) Disc gel electrophoresis

The relative movement of the enzyme of the present invention to bromophenol blue (hereinafter referred to as BPB) was measured by a disc gel electrophoresis measurement of a 7.5% polyacrylamide gel (pH 8.9). The relative movement ($R_mBPB$) of the enzyme of the present invention to BPB is from 0.125 to 0.167.

(9) Influence of metal ions

L-aminoacylase $S_1$ of the present invention is added to a 0.1 M Veronal buffer solution containing a final concentration of 1 mM of various metal salts, and left to stand at 37° C. for one hour. Then, it was reacted with N-Ac-DB-DOPS as the substrate at 37° C. for 1 hour, whereby the relative activity was measured by the above-mentioned method. The one where no metal was added, was evaluated to be 100%. The results are shown in Table 2.

TABLE 2

| Influence of metal ions | |
|---|---|
| Metal ions | Relative activity (%) |
| —(Control) | 100 |
| $Co^{++}$ | 162 |
| $Cu^{++}$ | 14 |
| $Ca^{++}$ | 72 |
| $Mg^{++}$ | 107 |
| $Zn^{++}$ | 102 |

TABLE 2-continued

| Influence of metal ions | |
|---|---|
| Metal ions | Relative activity (%) |
| $Mn^{++}$ | 61 |
| $Ag^+$ | 3 |
| $Hg^{++}$ | 2 |
| $Fe^{++}$ | 17 |
| $Ni^{++}$ | 7 |

Like many conventional amino acylases, L-aminoacylase $S_1$ of the present invention is activated by an addition of $Co^{++}$, and its activity is strongly inhibited by an addition of $Ni^{++}$, $Fe^{++}$, $Ag^{++}$, $Hg^{++}$ or $Cu^{++}$.

(10) Influence of inhibitors

The enzyme of the present invention is left to stand at 37° C. for one hour together with various inhibitors, and then reacted with N-Ac-DB-DOPS as the substrate at 37° C. for one hour, whereby the remaining activity was measured by the above-mentioned method. The results are shown in Table 3.

TABLE 3

| Influence of inhibitors | | |
|---|---|---|
| Inhibitor | Concentration | Remaining activity (%) |
| p-chloromercuribenzoate | 1 mM | 2 |
| Monoiodoacetic acid | 1 mM | 94 |
| Ethylenediaminetetraacetate | 1 mM | 72 |
| β-mercaptoethanol | 1 mM | 76 |

L-aminoacylase $S_1$ of the present invention is inhibited by p-chloromercuribenzoate as a SH inhibitor, but is not inhibited by monoiodoacetic acid. Further, it is moderately inhibited by ethylenediaminetetraacetate as a chelating agent.

Now, the physicochemical characteristics of L-aminoacylase $S_2$ will be described.

(1) Substrate profile

The enzymatic activity was measured by using N-acyl derivatives of various amino acids as the substrate. The relative activity based on L-N-acetyl-methionine being evaluated to be 100 is shown in Table 4.

TABLE 4

| Substrate profile | |
|---|---|
| Substrate | Relative activity (%) |
| L-N—acetyl-methionine | 100 |
| L-N—formyl-methionine | 5 |
| L-N—benzoyl-methionine | 10 |
| D-N—acetyl-methionine | 0 |
| N—acetyl-glycine | 2 |
| L-N—acetyl-alanine | 8 |
| L-N—acetyl-valine | 35 |
| L-N—acetyl-leucine | 71 |
| L-N—acetyl-tryptophan | 98 |
| D-N—acetyl-tryptophan | 0 |
| L-N—acetyl-phenylalanine | 286 |
| L-N—acetyl-tyrosine | 137 |
| L-N—acetyl-glutamic acid | 18 |
| L-N—acetyl-histidine | 36 |
| L-N—acetyl-arginine | 61 |
| L-threo-N—acetyl-3-(3,4-dibenzyloxyphenyl)serine | 20 |
| L-N—acetyl-2-(4-hydroxymethyl-3-hydroxyphenyl)glycine | 65 |
| DL-N—acetyl-α-methylbenzylamine | 0 |
| N—acetyl-D-glucosamine | 0 |

As is evident from Table 4, L-aminoacylase $S_2$ of the present invention acts on N-acyl derivatives of a wide range of L-amino acids including special synthetic amino acids. On the other hand, acylases usually act preferentially on such acyl groups as an acetyl group and a chloroacetyl group, but rarely hydrolyzes e.g. a benzoyl group. Some acylases produced by a certain group of bacteria act selectively on a benzoyl group, but such acylases do not hydrolyze e.g. an acetyl group. Whereas, L-aminoacylase $S_2$ of the present invention shows a wide substrate profile for various acyl groups. While it acts most effectively on e.g. an acetyl group and a chloroacetyl group, but it is also effective to readily hydrolyze a benzoyl group.

(2) Thermal stability

A potassium phosphate buffer solution (pH 7.0) of the enzyme of the present invention was treated for 10 minutes at various temperatures, whereupon the remaining activity was measured.

Figure 5:
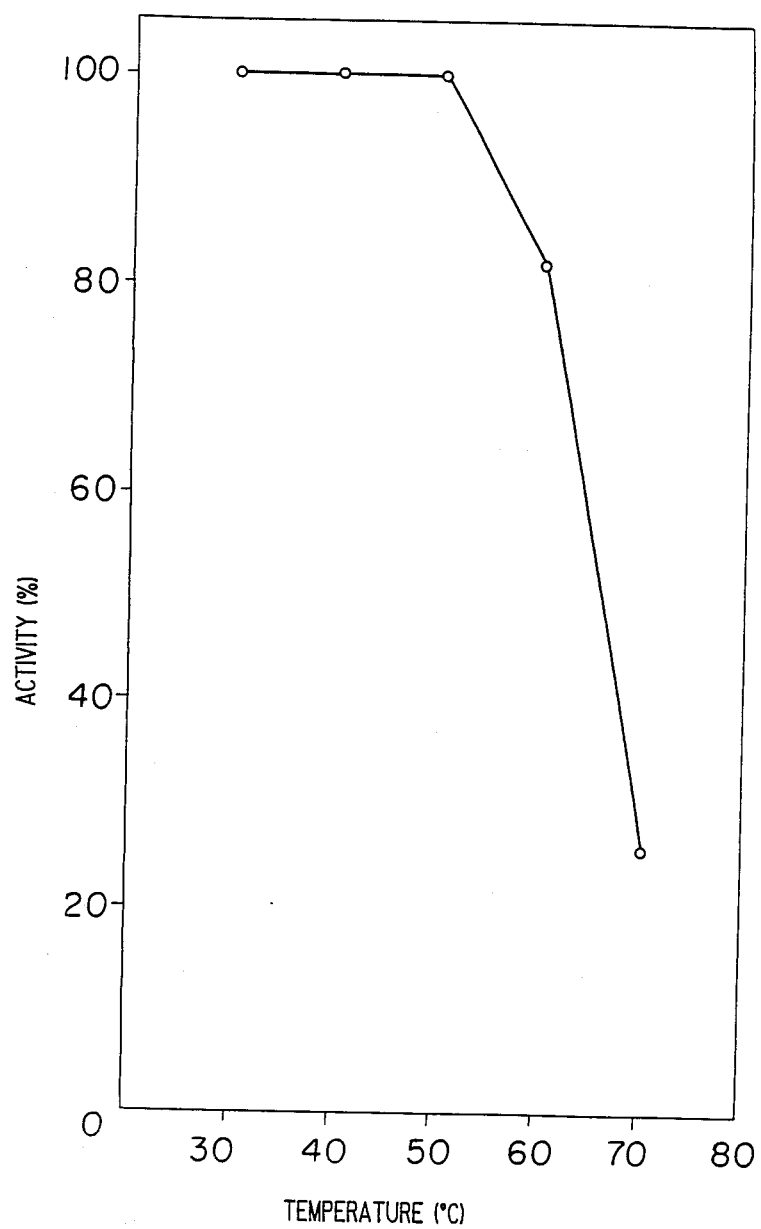
FIG. 5 shows the thermal stability of L-aminoacylase $S_2$ of the present invention.

As the substrate, N-Ac-DB-DOPS was used, and the reaction was conducted at 37° C. for one hour, whereby freed DB-DOPS was measured by a ninhydrin method to determine the enzymatic activity. The results of the measurements are shown in FIG. 5. As shown in the Figure, 20% is deactivated by the treatment at 60° C., and at least 70% is deactivated at 70° C. However, the enzyme is certainly stable at 50° C.

(3) Temperature-dependence

Figure 6:
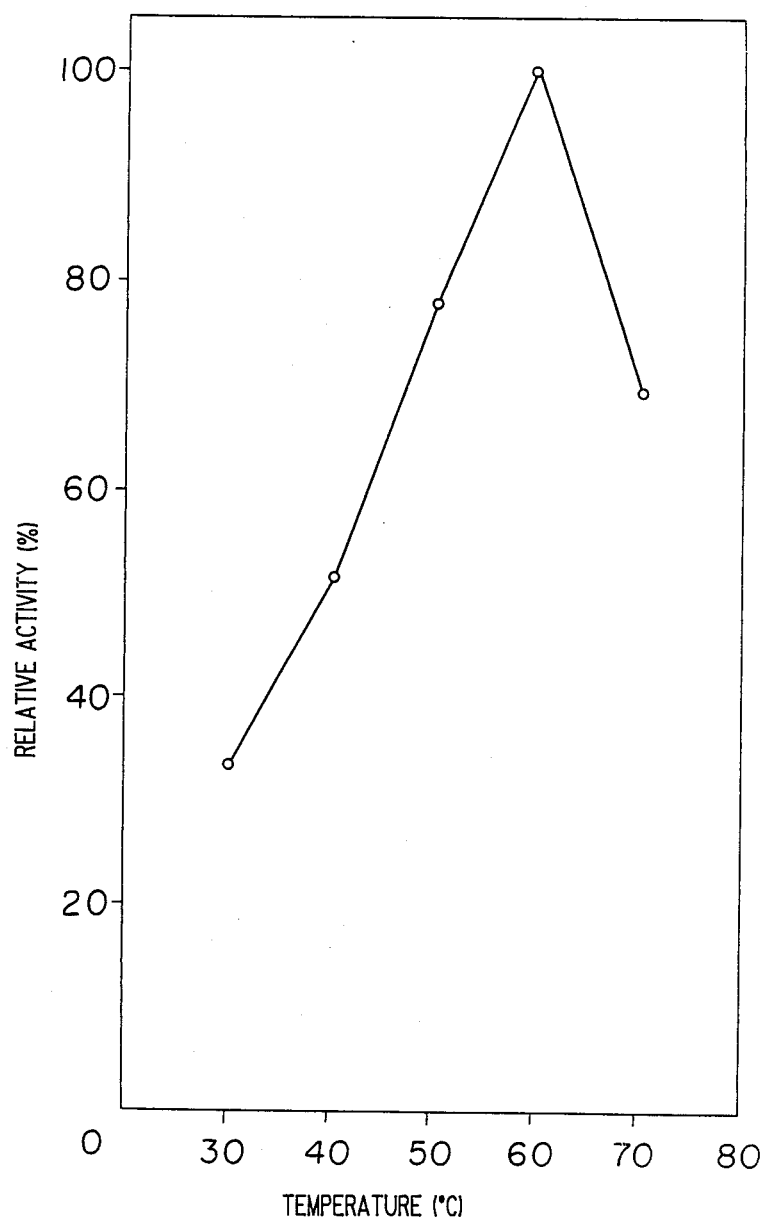
FIG. 6 shows its reaction temperature (optimum temperature).

The enzyme of the present invention was reacted in a potassium phosphate buffer solution (pH 7.0) with N-Ac-DB-DOPS as the substrate for 10 minutes under various temperature conditions, whereby the relative activity was measured by the above-mentioned method. The results are shown in FIG. 6. As the results show, the reactivity increases almost linearly up to about 60° C., and even at 70° C., the activity does not abruptly decrease.

(4) pH stability

Figure 7:
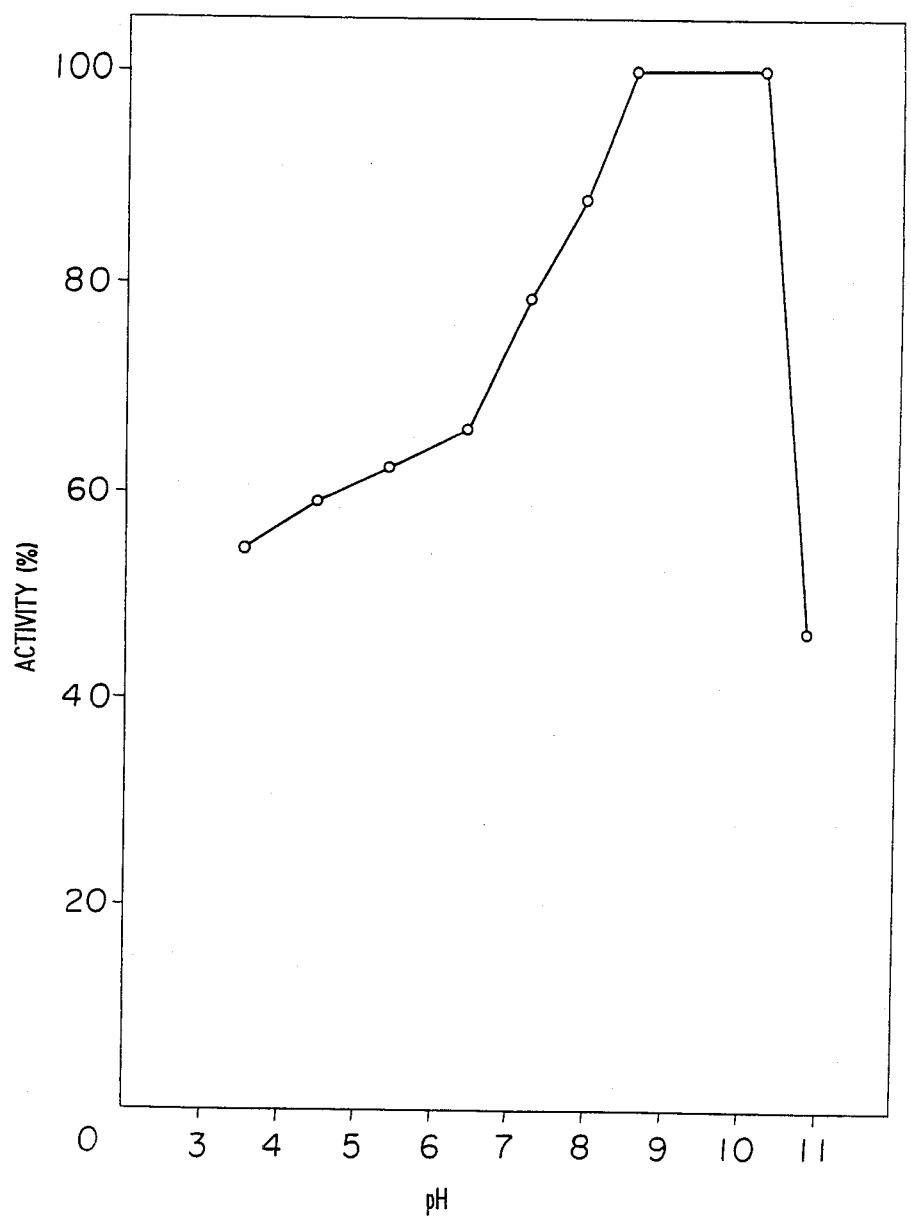
FIG. 7 shows its pH stability.

The enzyme solution of the present invention was left to stand at 5° C. for 24 hours under various pH conditions. Then, each solution was adjusted to pH 7.0, and then reacted with N-Ac-DB-DOPS as the substrate at 37° C. for one hour, whereupon the remaining activity was measured by the above-mentioned method. The results are shown in FIG. 7. L-aminoacylase $S_2$ of the present invention is most stable under a weakly basic condition i.e. at pH 8-10.

(5) pH-dependence

Figure 8:
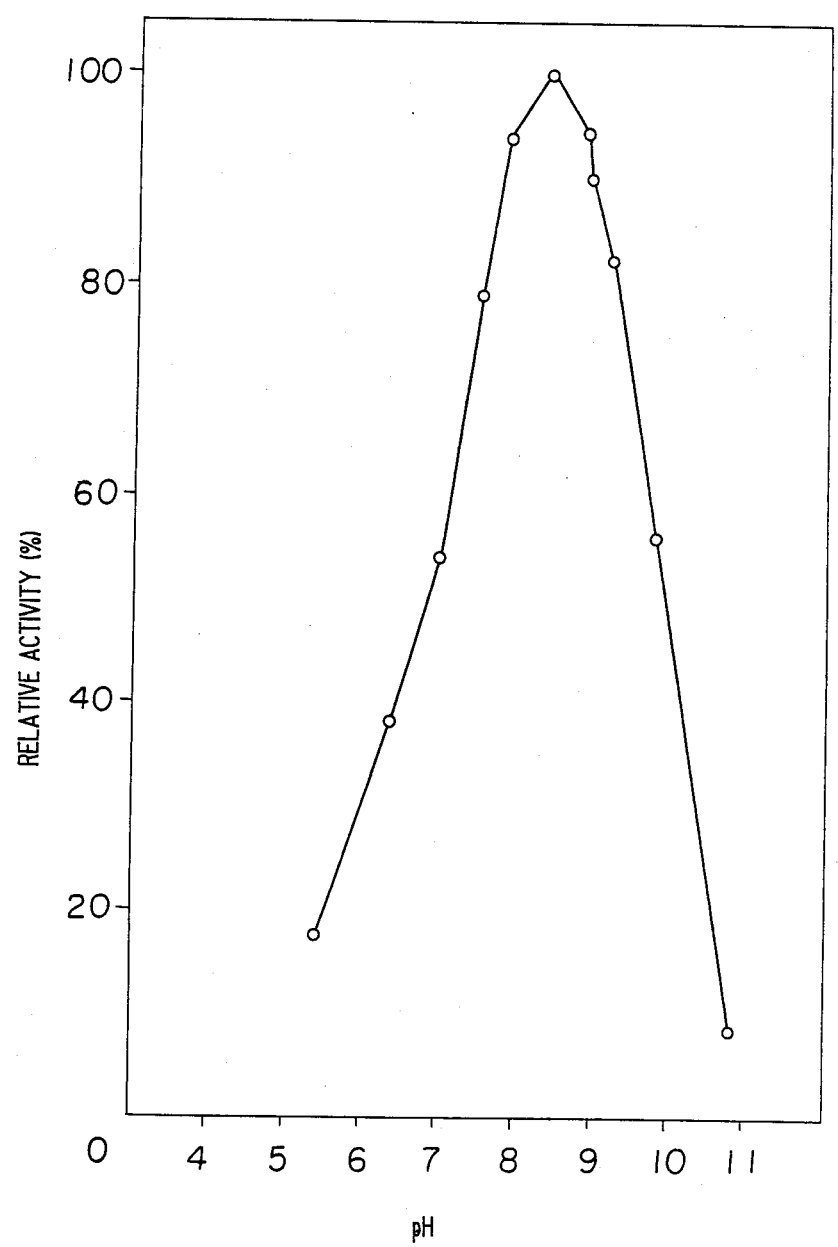
FIG. 8 shows its reaction pH (optimum pH).

The enzyme of the present invention was reacted for one hour with N-Ac-DB-DOPS as the substrate at 37° C. under various pH conditions, and the relative activity was measured by the above-mentioned method. The results are shown in FIG. 8. L-aminoacylase $S_2$ of the present invention is highly reactive at pH 7.0-10.0, and the optimum pH is from about 8.0 to about 9.0.

(6) Molecular weight

The molecular weight of the enzyme of the present invention was measured by a gel-filtration method of Sephadex G-100 ® (manufactured by Pharmacia Company). As the results, the molecular weight of L-aminoacylase $S_2$ of the present invention was found to be within a range of from 50,000 to 60,000 Dalton.

As standard protein samples, cytochrome C (molecular weight: 12,500), carbonic anhydrase (molecular weight: 29,000), egg white albumin (molecular weight: 45,000) and bovine serum albumin (molecular weight: 67,000) were used.

(7) Isoelectric point

The isoelectric point of L-aminoacylase $S_2$ of the present invention was measured at 4° C. by applying 800 V for two hours by using Anpholine PAG ® plate (manufactured by LKB Company).

The isoelectric point (pI) of the enzyme of the present invention is within a range of from 6.38 to 7.42.

(8) Disc gel electrophoresis

The relative movement of the enzyme of the present invention to BPB was measured by a disc gel electrophoresis of a 7.5% polyacrylamide gel (pH 8.9). The relative movement ($R_m$BPB) of the enzyme of the present invention to BPB is from 0.180 to 0.280.

(9) Influence of metal ions

L-aminoacylase $S_2$ of the present invention was added to 0.1 M Veronal buffer solution containing as the final concentration 1 mM of various metal salts, and the reaction was conducted at 37° C. for 1 hour. Then, it was reacted with N-Ac-DB-DOPS as the substrate at 37° C. for one hour, whereupon the relative activity was measured by the above-mentioned method. The activity of the one where no metal salt was added, was evaluated to be 100%. The results of the measurements are shown in Table 5.

TABLE 5

| Influence of metal ions | |
|---|---|
| Metal ions | Relative activity (%) |
| —(Control) | 100 |
| $Co^{++}$ | 38 |
| $Cu^{++}$ | 16 |
| $Ca^{++}$ | 98 |
| $Mg^{++}$ | 95 |
| $Zn^{++}$ | 71 |
| $Mn^{++}$ | 31 |
| $Ag^+$ | 0 |
| $Hg^{++}$ | 15 |
| $Fe^{++}$ | 18 |
| $Ni^{++}$ | 33 |

L-aminoacylase $S_2$ of the present invention is prohibited by metal ions such as $Co^{++}$, $Ni^{++}$, $Mn^{++}$, $Hg^{++}$, $Fe^{++}$, $Cu^{++}$ and $Ag^+$.

(10) Influence of inhibitors

The enzyme of the present invention was left to stand for one hour at 37° C. together with various inhibitors, and then reacted at 37° C. for one hour with N-Ac-DB-DOPS as the substrate, whereupon the remaining activity was measured by the above-mentioned method.

The results are shown in Table 6.

TABLE 6

| Influence of inhibitors | | |
|---|---|---|
| Inhibitor | Concentration | Remaining activity (%) |
| p-chloromercuribenzoate | 1 mM | 0 |
| L-cysteine | 1 mM | 11 |
| Monoiodoacetic acid | 1 mM | 3 |
| Ethylenediaminetetraacetate | 1 mM | 92 |

L-aminoacylase $S_2$ of the present invention is strongly inhibited by p-chloromercuribenzoate and monoiodoacetic acid as a SH inhibitor, and is scarcely inhibited by ethylenediaminetetraacetate as the chelating agent. L-aminoacylase $S_2$ of the present invention is also inhibited by cysteine as an amino acid having a SH group.

Further, conventional L-aminoacylases and L-aminoacylases of the present invention were compared in the substrate profiles and the thermal stability.

(A) Substrate profiles

The substrate profiles of L-aminoacylase $S_1$ and L-aminoacylase $S_2$ of the present invention and conventional L-aminoacylases were measured. The results are shown in Table 7.

TABLE 7

| Comparison of substrate profiles | | | |
|---|---|---|---|
| | Substrate | | |
| Enzyme (source) | L-N—acetyl-methionine | D-N—acetyl-methionine | L-threo-N—acetyl-3-3,4-dibenzyl-oxyphenyl) serine |
| L-aminoacylase $S_1$ (St. hachijoensis) | + | — | + |
| L-aminoacylase $S_2$ (St. rimofaciens) | + | — | + |
| Acylase Amano (Aspergillus sp.) | + | — | — |
| Acylase Tokyo kasei (Aspergillus genus) | + | — | — |
| Acylase I (hog kidney) | + | — | — |

+: active
—: inactive

L-aminoacylase $S_1$ and L-aminoacylase $S_2$ of the present invention was compared with commercially available L-aminoacylases in their activity by using N-acetyl derivatives of D- or L-methionine and L-threo-3-(3,4-dibenzyloxyphenyl) serine as substrates. The conventional L-aminoacylases were found to act only on the L-derivatives, and only the enzymes of the present invention were found to be active against the special substrate such as L-threo-N-acetyl-3-(3,4-dibenzyloxyphenyl)serine.

(B) Thermal stability

L-aminoacylase $S_1$ and L-aminoacylase $S_2$ of the present invention were compared in their thermal stability.

Figure 9:
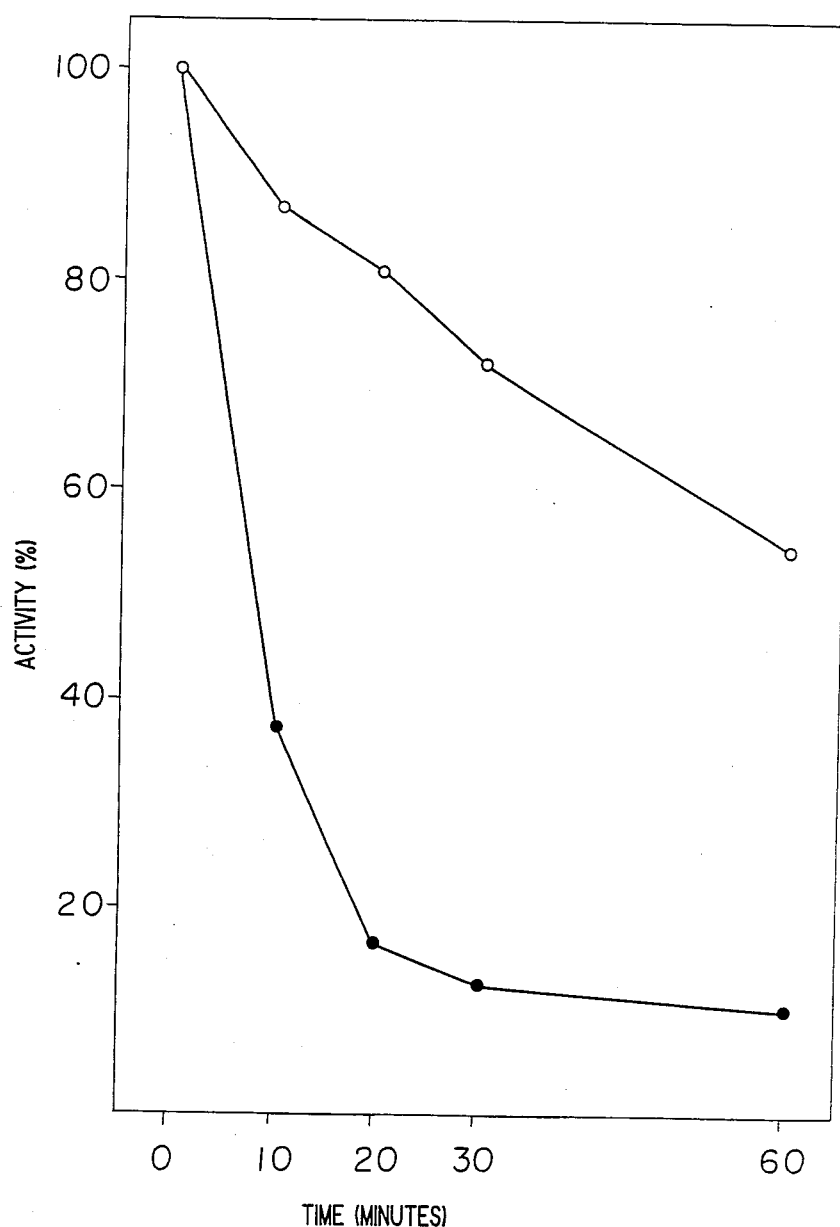
FIG. 9 illustrates a comparison in the thermal stability of L-aminoacylase $S_1$ (●—●) and L-aminoacylase $S_2$ (○—○).

Method for Measurement 0.5 ml of each enzyme solution (pH 7.0) was subjected to heat treatment at 60° C. for various predetermined periods of time. After cooling the solution with ice, 0.5 ml of a 0.02 M N-Ac-DB-DOPS solution as the substrate was added, and the mixture was left to stand at 37° C. for one hour. Then, DB-DOPS was measured by a ninhydrin method to determine the activity. The results are shown in FIG. 9.

As is evident from the above results, L-aminoacylase $S_2$ of the present invention has a substrate profile wider than the conventional acylases, like L-aminoacylase $S_1$. While L-aminoacylase $S_2$ of the present invention has substantially the same substrate profile as L-aminoacylase $S_1$, L-aminoacylase $S_2$ of the present invention is superior to L-aminoacylase $S_1$ in the thermal stability.

The L-aminoacylase-producing microorganism to be used in the present invention, may be any wild strain, variety or recombined strain obtained by cell fusion, by genetic recombination or any other genetic engineering, so long as it is a microorganism belonging to actinomycetes capable of producing L-aminoacylase $S_1$ or L-aminoacylase $S_2$ of the present invention. For instance, as specific examples of microorganisms having an ability to produce L-aminoacylase $S_1$, there may be mentioned *Actinomyces aureoverticillatus*, IMC S-0234 (ISP 5080) (FERM P-7216); Actinomyces bicolor, IMC S-0276 (ISP 5140); *Streptomyses blastmycetics*, IMC S-0189 (ISP 5029) (FERM P-7217); *Streptomyces chartreusis*, IMC S-0226 (ISP 5085); *Streptomyces flavopersicus*, IMC S-0204 (ISP 5093); *Actinomyces flavotricini*, IMC S-0219 (ISP 5152); *Streptoverticillium griseocarneum*, IMC S-0237 (ISP 5004); *Streptomyces hachijoensis*, IMC S-0244 (ISP 5114) (FERM P-7218); *Streptomyces halstedii*, IMC S-0194 (ISP 5068); *Streptoverticillium hiroshimense*, IMC S-0179 (ISP 5037) (FERM P-7252); *Streptomyces tendae*, IMC S-0168 (ISP 5101); and *Streptomyces toyocaensis*, IMC S-0163 (ISP 5030) (FERM P-7253). These strains are all known strains disclosed in literatures. Among the above strains, the strains identified with FERM P-7216, FERM P-7217 and FERM P-7218 were deposited on Sept. 5, 1983 and the strains identified with FERM P-7252 and FERM P-7253 were deposited on Sept. 20, 1983, respectively, at the Japanese depository "Fementation Research Institute", Agency of Industrial Science and Technology, Japan. As a specific example of the strain having an ability to produce L-aminoacylase $S_2$ of the present invention, there may be mentioned, for instance, *Streptoverticillium rimofaciens*, MH240-CPF7. This *Streptoverticillium rimofaciens* MH240-CPF7 is a strain isolated by the present inventors from a soil in Omiya-machi, Ibaraki-ken, Japan, and its micrological characteristics are as shown below.

Micrological characteristics of *Streptoverticillium rimofaciens*

1. Morphology

As observed under microscope, MH240-CPF7 strain has aerial mycellia extending from a branched in-substrate mycellium and having cyclic branches. A chain of at least 10 spores is observed at the forward end of each aerial mycellium, but no spiralization is observed. The size of each spore is about 0.6×0.8–1.4 μm, and the surface of each spore is smooth.

2. Growth on various culture media (1) Sucrose nitrate agar culture medium (incubated at 27° C.)

Slightly white aerial mycellia form on colorless growth, and no soluble pigment is observed.

(2) Glucose asparagine agar culture medium (incubated at 27° C.)

Slightly white aerial mycellia form on light yellow brown (2 gc, Bamboo) growth, and no soluble pigment is observed.

(3) Glycerol asparagine agar culture medium (ISP-culture medium 5, incubated at 27° C.)

Slightly white aerial mycellia form on light yellow brown (2 le, Mustard) growth, and no soluble pigment is observed.

(4) Starch inorganic salt agar culture medium (ISP-culture medium 4, incubated at 27° C.)

Slightly white aerial mycellia form on light yellow brown (2 le, Mustard) growth, and no soluble pigment is observed.

(5) Tyrosine agar culture medium (ISP-culture medium 7, incubated at 27° C.)

White or brownish white aerial mycellia form on light yellow brown (2 le, Mustard) growth. A soluble pigment is present to such an extent that a slight brown color is observed.

(6) Nutrient agar culture medium (incubated at 27° C.)

Growth is light yellow brown (2 ng, Dull Gold) and no aerial mycellia form. A soluble pigment is present to such an extent that a slight brown color is observed.

(7) Yeast malt agar culture medium (ISP-culture medium 2, incubated at 27° C.)

Yellow white or brown white aerial mycellia form on yellow brown (3 le, Cinnamon) growth. A soluble pigment is present to such an extent that a slight brown color is observed.

(8) Oatmeal agar culture medium (ISP-culture medium 3, incubated at 27° C.)

Brown white (3 ba, Pearl) aerial mycellia form on light yellow brown (2 le, Mustard) growth. A soluble pigment is present to such an extent that a slight brown color is observed.

(9) Glycerol nitrate agar culture medium (incubated at 27° C.)

Slightly white aerial mycellia form on colorless growth, and no soluble pigment is observed.

(10) Starch agar culture medium (incubated at 27° C.)

White aerial mycellia form on light brown (2 gc, Bamboo) growth, and no soluble pigment is observed.

(11) Calcium malate agar culture medium (incubated at 27° C.)

Slightly white mycellia form on colorless growth, and no soluble pigment is observed.

(12) Cellulose culture medium (filter paper-added synthetic solution, incubated at 27° C.)

Slightly white mycellia form on colorless growth, no soluble pigment is observed.

(13) Gelatin stab culture

In a simple 15% gelatin culture medium (incubated at 20° C.), growth was light yellow brown, no aerial mycellia form, and a brown soluble pigment is produced.

In a glucose-peptone-gelatin culture medium (incubated at 27° C.), growth is light brown, no aerial mycellia form, and a brown soluble pigment is produced.

(14) Skimmilk (incubated at 37° C.)

Growth was colorless or light brown, no aerial mycellia form, and a soluble pigment is present to such an extent that a slight brown color is observed.

The color standard indicated in a bracket ( ) in the above description is based on the color harmony manual of Container Corporation of America.

3. Physiological characteristics (1) Growth temperature range

Tests were conducted at temperatures of 20° C., 24° C., 27° C., 30° C. and 50° C. by using a glucose-asparagine agar culture medium (glucose: 1%, asparagine: 0.5%, $K_2HPO_4$: 0.5%, string agar: 3.0%, pH 7.0). As the results, growth was observed at each temperature except for 50° C. The optimum growth temperature is believed to be from about 27° C. to about 37° C.

(2) Liquefaction of gelatin (simple 15% gelatin culture medium, incubated at 20° C.; glucose-peptone-gelatin culture medium, incubated at 27° C.)

No liquefaction was observed in the simple gelatin culture medium. In the case of the glucose-peptone-gelatin culture medium, very slight liquefaction started from about 14 days after the initiation of the incubation.

(3) Hydrolysis of starch (starch-inorganic salt agar culture medium; starch agar culture medium, each incubated at 27° C.)

In each of the starch-inorganic salt agar culture medium and the starch agar culture medium, the hydrolysis of starch was observed after about seven days from the initiation of the incubation, but the action was relatively weak.

(4) Coagulation and peptonization of skimmilk (skimmilk, incubated at 37° C.)

Coagulation started after about five days from the initiation of the incubation and completed after about two weeks, and immediately peptonization started. The action was relatively weak.

(5) Formation of a melanine-like pigment (Tryptone-yeast broth, ISP-culture medium 1; pepsin-yeast-iron-agar, ISP-culture medium 6; tyrosine, ISP-culture medium 7, each incubated at 27° C.)

The formation was positive in the Tryptone-yeast broth, the peptone-yeast broth and the peptone-yeast-iron-agar culture medium, and is negative in the tyrosine agar culture medium.

(6) Utilization of carbon sources (pridoham gotolieve agar culture medium, ISP-culture medium 9, incubated at 27° C.)

The strain grew by utilizing D-glucose, D-fructose, inositol and D-mannitol. L-arabinose, D-xylose, sucrose, L-rhamnose and raffinose were not utilized.

(7) Dissolution of calcium malate (calcium malate agar culture medium, incubated at 27° C.)

Negative.

(8) Nitrate reduction (Peptone water containing 0.1% potassium nitrate, ISP-culture medium 8, incubated at 27° C.)

Negative.

The above characteristics may be summarized as follows.

Namely, the aerial mycellia of MH240-CPF7 strain have cyclic branches, and no spiralization is observed. The surface of spores is smooth. White or brownish white aerial mycellia form on light yellow brown growth in various culture media, and no soluble pigment is observed, or a pigment forms only to such an extent that a slight brown color is observed. The formation of a melanine-like pigment is positive in the tryptone-yeast broth and in the peptone-yeast-iron agar culture medium, and is negative in the tyrosine agar culture medium. The abilities for decomposing protein and for hydrolyzing starch are rather weak. Further, 2,6-diaminopimelic acid contained in the cell wall is of LL-type.

From these characteristics, MH240-CPF7 strain is believed to belong to genus Streptoverticillium. Further, from the investigation of analogous known strains, there may be mentioned *Streptomyces rimofaciens* (see Japanese Examined Patent Publication No. 7598/1967).

*Streptomyces rimofaciens* obtained from JCM was compared with MH240-CPF7 strain. The results are shown in Table 8.

TABLE 8

Comparison between the L-aminoacylase $S_2$-producing strain of the present invention and the known strain in the mycological characteristics

|  | MH240-CPF7 | Streptomyces rimofaciens IMC S-0729 (JCM4880) |
|---|---|---|
| Formation of cyclic branches | + | + |
| Spore surface | Smooth | Smooth |
| Color of aerial mycellia | White or brownish white | White or yellow white or brownish white |
| Color of growth | Light brown | Light brown |
| Soluble pigment | Negative or slight brown | Negative or slight brown |
| Formation of melanine-like pigment | | |
| ISP culture medium 1 | + | + |
| ISP culture medium 6 | + | + |
| ISP culture medium 7 | − | − |
| Hydrolysis of starch | + (weak) | + (weak) |
| Coagulation of milk | + | + |
| Peptonization | + (weak) | + (weak) |

TABLE 8-continued

Comparison between the L-aminoacylase $S_2$-producing strain of the present invention and the known strain in the mycological characteristics

| of milk | | |
|---|---|---|
| Liquefaction of gelatin | | |
| Simple gelatin | − | − |
| Glucose-peptone-gelatin | + (weak) | + (weak) |
| Reduction of nitrate | − | − |
| Utilization of carbon sources | | |
| D-glucose | + | + |
| L-arabinose | − | − |
| D-xylose | − | − |
| D-fructose | + | + |
| sucrose | − | − |
| inositol | + | + |
| L-rhamnose | − | − |
| raffinose | − | − |
| D-mannitol | + | + |
| Antibiotics produced | Destomycin | Destomycin |

As is evident from Table 8, the characteristics of MH240-CPF7 strain agree very much with the characteristics of *Streptomyces rimofaciens*. According to the description of the mycological characteristics of *Streptomyces rimofaciens* in Japanese Examined Patent Publication No. 7598/1967, a Czapek culture medium was used for the test of utilization of carbon sources because the strain did not grow on a pridoham-gotolieve culture medium. However, in this comparative test, the two strains grew on a pridoham-gotolieve culture medium, and the evaluation of the utilization of sucrose was easy. In addition, both strains produce antibiotic Destomycin, which indicates that the two strains are of the same species. Thus, MH240-CPF7 strain was identified as *Streptoverticillium remofaciens* MH240-CPF7 strain. MH240-CPF7 strain is deposited under accession number 8599 (FERM P-8599) at the Japanese depository "Fementation Research Institute", Agency of Industrial Science and Technology, Japan.

L-aminoacylase $S_1$ and L-aminoacylase $S_2$ of the present invention may be produced as follows.

L-aminoacylase $S_1$ and L-aminoacylase $S_2$ of the present invention are obtained by inoculating and aerobically culturing an optional L-aminoacylase-producing actinomycete strain on a culture medium containing nutrient sources. As the nutrient sources, those commonly known as nutrient sources for bacteria and actinomycetes may be employed. For instance, as the carbon source, there may be employed commercially available hydrocarbons such as glycerin, glucose, lactose, cane sugar, starch, maltose and molasses, vegetable oils such as soybean oil and cotton oil, and animal fats. As the nitrogen source, commercially available peptone, meat extract, cornsteep liquor, Corngluten meal ®, Pharmamedia ®, soybean powder, peanut powder, yeast extract, N-Z-amine, casein, sodium nitrate and ammonium sulfate may be mentioned. As the inorganic salt, sodium chloride, a phosphate, calcium carbonate and magnesium sulfate may be mentioned. Additionally, very small amounts of metal salts may be added, as the case requires. These sources may be employed so long as they are useful for the production of L-aminoacylase $S_1$ or L-aminoacylase $S_2$ of the present invention.

The incubation temperature may be at any level within a range where L-aminoacylase $S_1$ or L-aminoacylase $S_2$ of the present invention is produced, preferably from 20° to 30° C. The incubation period is usually from one day to ten days, and it is preferred to conduct the culturing aerobically.

The pH value for the incubation may be at any level so long as L-aminoacylase $S_1$ or L-aminoacylase $S_2$ is produced, but preferably within a range of pH 7.0–8.0.

L-aminoacylase $S_1$ and L-aminoacylase $S_2$ of the present invention are likely to be discharged out of the cells, and exist mainly in the culture medium.

Accordingly, as opposed to the preparation of other common fungal L-aminoacylases, in the case of L-aminoacylase $S_1$ and L-aminoacylase $S_2$ of the present invention, the respective filtered culture media may be employed by themselves as enzyme solutions without destroying the cells and extracting the enzymes therefrom. Further, if necessary, the enzymes of the present invention can be purified by usual biochemical methods. Namely, they may be purified by a proper combination of methods such an ammonium sulfate precipitation method, a membrane concentration method, a Column-lite ® (manufactured by Fuji Chemical Company) chromatography, an ion exchange chromatography, a gel chromatography and an electrophoresis.

Now, the present invention will be described in further detail with reference to Examples. However, it should be understood that the present invention is by no means restricted by these specific Examples.

EXAMPLE 1

*Streptomyces hachijoensis* IMC S-0244 (ISP-5114) (FERM-P-7218) i.e. one of the L-aminoacylase $S_1$-producing strains of the present invention, was inoculated to 100 ml of a culture medium in a 500 ml Erlenmeyer flask containing 1.0% of starch, 1.0% of glucose, 0.75% of meat extract, 0.75% of polypeptone, 0.3% of sodium chloride, 0.1% of magnesium sulfate, 0.007% of copper sulfate, 0.001% of ferrous sulfate, 0.0008% of manganese chloride and 0.0002% of zinc sulfate, and incubated at 27° C. for four days by shaking culture to obtain a seed culture. In the same manner with the same culture medium composition, 100 Erlenmeyer flasks each having a capacity of 500 ml were prepared, and 2 ml of the seed culture from the above seed culture flask was added to each flask. Then, the flasks were incubated at 28° C. for 4 days by shaking culture. The contents of the flasks were put together, and microbial cells were removed by filtration under suction to obtain 7.5 l of the filtrate. The culture filtrate was concentrated to 400 ml by an ultrafiltration module (ACL-1010, manufactured by Asahi Chemical Company). To the concentrated solution, 200 ml of a 0.02 M potassium phosphate buffer solution (pH 7.0) was added, and the mixture was again concentrated to 300 ml by the above-mentioned ultrafiltration module. This operation was repeated twice, and then the inner solution was forcibly pushed out with the above buffer solution to obtain 0.63 l of a crude enzyme solution.

The activity of the L-aminoacylase was determined by the reaction at 37° C. for one hour by using L-threo-N-acetyl-3-(3,4-dibenzyloxyphenyl)serine as the substrate, followed by the measurement of the resulting L-threo-3-(3,4-dibenzyloxyphenyl)serine by a ninhydrin method. Namely, the reaction was terminated by adding 1 N hydrochloric acid to the system to modify the enzyme, and the resulting L-threo-3-(3,4-dibenzyloxyphenyl)serine was transferred to butanol from the system. The butanol extract solution was developed by a ninhydrin method, and the absorbance at 570 nm was measured by colorimetry. When the activity of L-aminoacylase giving the freed acetyl derivative concentration of 100 μg/ml is defined to be 1 unit, the above crude enzyme solution had $5.92 \times 10^4$ units. The overall recovery rate was at least 98%.

EXAMPLE 2

400 ml of the crude enzyme solution ($3.76 \times 10^4$ units) prepared in Example 1 was passed through a column (inner diameter: 3.7 cm, height: 30 cm) of Column-lite ® (manufactured by Fuji Chemical Industries Company Ltd.) which was preliminarily equilibrated with a 5 mM potassium phosphate buffer solution (pH 7.0), whereby L-aminoacylase $S_1$ was adsorbed. By passing 200 ml of the above buffer solution, the column was washed with the buffer solution, and then by increasing the concentration of the buffer solution linearly up to 0.5 M, L-aminoacylase $S_1$ was eluted.

L-aminoacylase $S_1$ of the present invention was eluted with a 0.2–0.3 M potassium phosphate buffer solution (pH 7.0), and the active fractions were collected and subjected to dialysis against a 5 mM potassium phosphate buffer solution (pH 7.0, 5° C.) to obtain 200 ml of a purified enzyme solution. The overall recovery rate was 80%, and the specific activity was increased by about 11 times.

EXAMPLE 3

The enzyme solution purified by Example 2 can further be purified by e.g. an ion exchange Sephadex. Namely, the enzyme solution was passed through a column (inner diameter: 3.0 cm, height: 25.0 cm) of CM-Sephadex C-50 ® (manufactured by Pharmacia Company) which was preliminarily equilibrated with a 5 mM potassium phosphate buffer solution, whereby L-aminoacylase $S_1$ was adsorbed.

The column was washed by passing 800 ml of the above buffer solution, and then the active enzyme fractions were eluted by increasing the concentration of the buffer solution linearly.

L-aminoacylase $S_1$ of the present invention was eluted by a 0.08–0.12 M potassium phosphate buffer solution (pH 7.0). The overall recovery rate was 90%. The specific activity was increased by 7.3 times and 85 times over the enzyme solutions of the Example 2 and Example 1, respectively.

EXAMPLE 4

The enzyme solution purified in Example 3 can further be purified by DEAE-Sephadex A-50 ® (manufactured by Pharmacia Company). Namely, the enzyme solution containing 1200 units of the enzyme was passed through a column (inner diameter: 1.6 cm, height: 11.0 cm) of DEAE-Sephadex A-50 ® which was preliminarily equilibrated with a 5 mM potassium phosphate buffer solution, and then after washing the column with 100 ml of the above buffer solution, the active enzyme fractions were eluted by increasing the concentration of the buffer solution linearly.

L-aminoacylase $S_1$ of the present invention was eluted by a 0.2–0.25 M potassium phosphate buffer solution (pH 7.0). The overall recovery rate was 85%. The specific activity was increased by 1.7 times over that of Example 3.

EXAMPLE 5

With respect to the purified enzyme obtained in Example 4, gel filtration was conducted by using Sephadex G-100 ® (manufactured by Pharmacia Company). 0.2 mg calculated as albumin of the purified enzyme obtained in Example 4 and 1.0 ml of a 0.5% glycerol solution containing 0.5-1 mg of one of various protein standard samples, were passed through a column (inner diameter: 1.7 cm, height: 81.5 cm) of Sephadex G-100 ® which was preliminarily equilibrated with a 50 mM potassium phosphate buffer solution. The eluate was collected in portions of 2.0 ml by fraction collectors by passing the above buffer solution at flow rate of 3.6 ml/hr. The enzymatic activity was determined by the quantitative analysis of the protein by a Lowry method of absorbance at 280 nm and the enzymatic activity. From the result of the gel chromatography, the purified enzyme was found to be a single protein band, and the molecular weight was found to be from 50,000 to 60,000 because it was eluted in about 1.4 times the void volume.

EXAMPLE 6

*Streptoverticillium rimofaciens* MH240-CPF7 strain i.e. the L-aminoacylase $S_2$-producing strain of the present invention, was inoculated under a sterile condition to 100 ml of a sterilized culture medium in a 500 ml of Erlenmeyer flask containing 3% of glucose, 1.5% of Pharmamedia ®, 0.3% of sodium chloride, 0.1% of magnesium sulfate, 0.007% of copper sulfate, 0.0001% of ferrous sulfate, 0.0008% of manganese chloride and 0.0002% of zinc sulfate, and incubated at 27° C. for 3 days by shaking culture, to obtain a seed culture. 1.5 l of the same culture medium as above was introduced into each of 18 Erlenmeyer flasks each having capacity of 5 l. After sterilization, 10 ml of the above seed culture was added to each flask, and incubated at 27° C. for 4 days by shaking culture. Then, the cultured media in the flasks were collected, and the microbial cells were removed by filtration under suction to obtain 19.6 l of a filtrate.

The culture filtrate thus obtained was passed through a column packed with 2 l of Column-lite ® (manufactured by Fuji Chemical Company) which was preliminarily equilibrated with a 5 mM potassium phosphate buffer solution (pH 7.0), whereby L-aminoacylase $S_2$ was adsorbed. The columm was washed with 7 l of water, and L-aminoacylase $S_2$ was eluted with 5 l of a 0.5 M potassium phosphate buffer solution (pH 7.0). The active fractions were collected to obtain 1.95 l of a crude enzyme solution. This crude enzyme solution had active units of $1.69 \times 10^5$ units, and the overall recovery rate was at least 95%.

The activity of this enzyme was determined by reacting it to L-threo-N-acetyl-3-(3,4-dibenzyloxyphenyl) serine as the substrate and measuring the resulting L-threo-3-(3,4-dibenzyloxyphenyl)serine by a ninhydrin method.

Namely, the substrate and the enzyme solution were added to a 0.1 M potassium phosphate buffer solution (pH 7.0) and reacted at 37° C. for one hour. Then, the reaction was terminated with hydrochloric acid, the resulting L-threo-3-(3,4-dibenzyloxyphenyl)serine was transferred to butanol. Then, the butanol extract solution was developed by a ninhydrin method, and the absorbance at 570 nm was measured by colorimetry.

The activity of L-aminoacylase $S_2$ giving the L-threo-3-(3,4-dibenzyloxyphenyl)serine concentration of 100 $\mu$g/ml is defined to be 1 unit.

EXAMPLE 7

540 g of ammonium sulfate was added to 1.95 l of the crude enzyme solution ($1.69 \times 10^5$ units) obtained in Example 6 to obtain a 45% saturated solution. The solution was passed through a column (inner diameter: 2.5 cm, height: 25 cm) packed with Toyopearl HW-65 ® (manufactured by Toyo Soda Manufacturing Co., Ltd.) which was preliminarily equilibrated with a 45% saturated ammonium sulfate solution, whereby L-aminoacylase $S_2$ was adsorbed.

Then, the column was washed with a 45% saturated ammonium sulfate solution, and then L-aminoacylase $S_2$ was eluted by passing a 35% saturated ammonium sulfate solution and then passing a 25% saturated ammonium sulfate solution. The active fractions were collected and subjected to dialysis against a 2 mM tris-hydrochloric acid buffer solution (pH 8.2) to obtain 440 ml of a purified enzyme solution (yield: at least 95%).

EXAMPLE 8

The enzyme solution obtained in Example 7 was passed through a column (inner diameter: 2 cm, height: 21.5 cm) of DEAE-Toyopearl 650 M ® (manufactured by Toyo Soda Manufacturing Co., Ltd.) which was preliminarily equilibrated with a 2 mM tris-hydrochloric acid buffer solution (pH 8.2), whereby L-aminoacylase $S_2$ was adsorbed. Then, L-aminoacylase $S_2$ was eluted by increasing the concentration of the tris-hydrochloric buffer solution (pH 8.2) from 5 mM to 200 mM linearly. The active fractions were collected to obtain 84 ml of a purified enzyme solution ($7.7 \times 10^4$ units) (yield: 59%).

EXAMPLE 9

84 ml of the purified enzyme solution (specific activity: $7.7 \times 10^4$ units) obtained in Example 8 was subjected to dialysis against water, and then passed through a column (inner diameter: 2 cm, height: 28 cm) of CM-Toyopearl 650 M ® (manufactured by Toyo Soda Manufacturing Co., Ltd.) which was preliminarily equilibrated with a 5 mM potassium phosphate buffer solution (pH 7.0). 60.9 g of ammonium sulfate was added to 215 ml of the eluate passed through the CM-Toyopearl 650 M column, and the mixture was passed through a column (inner diameter: 2 cm, height: 45 cm) of Toyopearl HW-56 ® (manufactured by Toyo Soda Manufacturing Co., Ltd.) which was preliminarily equilibrated with a 45% saturated ammonium sulfate solution, whereby L-aminoacylase $S_2$ was adsorbed. Then, L-aminoacylase $S_2$ was eluted by decreasing the concentration of the ammonium sulfate solution linearly. The active fractions were collected and subjected to dialysis against a 5 mM tris-hydrochloric acid buffer solution (pH 8.2) to obtain 105 ml of a purified enzyme solution (specific activity: 2323 units/280 nm absorbance) (yield: 46%).

L-aminoacylase $S_1$ and L-aminoacylase $S_2$ of the present invention can be produced in large amounts by the respective aminoacylase-producing strains in inexpensive culture media. Yet, they are discharged out of the microbial cells, whereby the culture filtrates can by themselves be used as enzyme solutions without requiring any special extraction operations. Further, particularly L-aminoacylase $S_2$ has a wide substrate profile and excellent heat resistance, and it is useful for optical resolution of not only natural amino acids but also synthetic amino acids. In addition, in such operation, there is no need for special means to prevent the contamination with microorganisms, and it is possible to increase the substrate concentration.

For example, by utilizing the characteristics of the enzymes of the present invention, the production of L-amino acids from N-acyl-L-amino acids and the optical resolution of N-acyl-D,L-amino acids can readily be conducted on an industrial scale. Accordingly, by using L-aminoacylase $S_1$ or L-aminoacylase $S_2$ of the present invention, the simplification and improvement in the efficiency of the industrial process for the production of optically active amino acids will be possible.

Further, L-aminoacylase $S_1$ and L-aminoacylase $S_2$ of the present invention have wider substrate profiles than the conventional L-aminoacylases. For instance, when L-aminoacylases of the present invention are acted on DL-threo-N-acetyl-3-(3,4-dibenzyloxyphenyl)serine to which Acylase Amano i.e. typical conventional acylase is not active, the enzymes of the present invention selectively hydrolyze acetyl amino groups of only the L-form of the compound, whereby it is possible to obtain L-threo-3-(3,4-dibenzyloxyphenyl)serine which is an intermediate for the synthesis of L-threo-3-(3,4-dihydroxyphenyl)-N-methylserine useful as a curing agent for the Parkinson disease.

We claim:

1. L-aminoacylase $S_1$ derived from an actinomycete and having the following physicochemical characteristics:

(1) Action and substrate profile:
It is a L-aminoacylase which acts on a N-acyl-L-amino acid to give a L-amino acid, its substrate profile is wide, and it acts not only on a N-acyl derivative of a natural L-amino acid, but also on a N-acyl derivative of a synthetic L-amino acid, while it does not act on a N-acyl-D-amino acid, a DL-N-acetyl-α-methylbenzylamine and a N-acetyl-D-glucosamine, (2) Stability
Temperature: it maintains its activity almost fully at 50° C., and a slight activity remains even at 60° C. (when left for one hour at pH 7.0),
pH: it is most stable at pH 7.0–9.0, and relatively stable even at about pH 10.0, but it loses its activity at pH 4.0 or lower (when left for 24 hours at 5° C.), (3) Temperature- and pH-dependence
Temperature: its activity increases linearly up to 50° C., and it loses its reactivity rapidly at a temperature of 60° C. or higher,
pH: its reactivity is high at pH 6.5–9.5 and the optimum pH for the reaction is about pH 7.5–8.5, (4) Molecular weight: 50,000–60,000 (gel-filtration method)

(5) Isoelectric point: pI=7.00–7.70, (6) Disc gel electrophoresis: $R_m$BPB=0.125–0.167

(7) Influence of metal ions
It is strongly inhibited by $Fe^{++}$, $Ni^{++}$, $Ag^+$, $Hg^{++}$ and $Cu^{++}$, and it is activated by $Co^{++}$, (8) Inhibitor
It is inhibited by p-chloromercuribenzoate, it is not inhibited by monoiodoacetic acid, and it is moderately inhibited by ethylenediaminetetraacetate.

2. L-aminoacylase $S_2$ derived from *streptoverticellium rimofaciens* MH 240-CPF7 or mutants and derivatives thereof, and having the following physiochemical characteristics:

(1) Action and substrate profile
It is a L-aminoacylase which acts on a N-acyl-L-amino acid to give a L-amino acid, its substrate profile is wide, and it acts not only on a N-acyl derivative of a natural L-amino acid, but also on a N-acyl derivative of a synthetic L-amino acid, while it does not act on a N-acyl-D-amino acid, a DL-N-acetyl-α-methylbenzylamine and a N-acetyl-D-glucosamine, (2) Stability
Temperature: it does not lose its activity up to 50° C., maintains 80% of the activity at 60° C., and at least 20% of the activity remains even at 70° C. (when left for 10 minutes at pH 7.0),
pH: it is most stable at pH 8.5–10.0, and 50% of the activity remains even at about pH 3.5 and at about pH 11.0 (when left for 24 hours at 5° C.), (3) Temperature- and pH-dependence
Temperature: its relative activity increases linearly up to 60° C., and it maintains at least 70% of the reactivity even at 70° C.,
pH: its reactivity is high at pH 7.0–10.0, the optimum pH for the reaction is about pH 8.0–9.0.

(4) Molecular weight: 50,000 to 60,000 (gel-filtration method), (5) Isoelectric point: pI=6.38–7.42

(6) Disc gel electrophoresis: $R_m$BPB=0.180–0.280

(7) Influence of metal ions
It is strongly inhibited by $Cu^{++}$, $Mn^{++}$, $Co^{++}$, $Hg^{++}$, $Fe^{++}$, $Ni^{++}$ and $Ag^+$, (8) Inhibitor
It is strongly inhibited by p-chloromercuribenzoate, L-cysteine and monoidoacetic acid, but it is substantially uninhibited by ethylenediaminetetraacetate.

3. The L-aminoacylase $S_1$ of claim 1, which is derived from an acetinomycete selected from the group of strains consisting of *Actinomyces aureoverticillatus*, IMC S-0234 (ISP 5080); Actinomyces bicolor, IMC S-0276 (ISP 5140); *Streptomyces blastmycetics*, IMC S-0189 (ISP 5029); *Streptomyces chartreusis*, IMC S-0226 (ISP 5085); *Streptomyces flavopersicus*, IMC S-0204 (ISP 5093); *Acetinomyces flavotricini*, IMC S-0219 (ISP 5152); *Streptoverticillium griseocarneum*, IMC S-0237 (ISP 5004); *Streptomyces hachijoensis*, IMC S-2044 (ISP 5114); *Streptomyces halstedii*, IMC S-[B 0194 (ISP 5068); *Streptoverticillium hiroshimense*, IMC S-0179 (ISP 5037); *Streptomyces tendae*, IMC S-0168 (ISP 5101); and *Streptomyces toyocaensis*, IMC S-0163 (ISP 5030).

* * * * *